United States Patent [19]

Gaster et al.

[11] Patent Number: 5,726,187
[45] Date of Patent: Mar. 10, 1998

[54] N-ALKYLPIPERIDINYL-4-METHYL CARBOXYLIC ESTERS/AMIDES OF CONDENSED RING SYSTEMS AS 5-HT4 RECEPTOR ANTAGONISTS

[75] Inventors: Laramie Mary Gaster, Bishop's Stortford; Graham Francis Joiner, Brentwood; Keith Raymond Mulholland, Harlow; Paul Adrian Wyman, Epping, all of England

[73] Assignee: SmithKline Beecham plc, Brentford, United Kingdom

[21] Appl. No.: 416,791

[22] PCT Filed: Oct. 14, 1993

[86] PCT No.: PCT/GB93/02130

§ 371 Date: Apr. 14, 1995

§ 102(e) Date: Apr. 14, 1995

[87] PCT Pub. No.: WO94/08965

PCT Pub. Date: Apr. 28, 1994

[30] Foreign Application Priority Data

| Oct. 16, 1992 | [GB] | United Kingdom | 9221766 |
| Nov. 5, 1992 | [GB] | United Kingdom | 9223136 |
| Nov. 5, 1992 | [GB] | United Kingdom | 9223140 |
| Mar. 12, 1993 | [GB] | United Kingdom | 9305141 |
| May 11, 1993 | [GB] | United Kingdom | 9309643 |

[51] Int. Cl.[6] ............ A61K 31/445; C07D 401/12
[52] U.S. Cl. ........................ 514/323; 546/200
[58] Field of Search .................. 514/323; 546/200

[56] References Cited

U.S. PATENT DOCUMENTS 5,049,556  9/1991  King et al. .............. 514/183

FOREIGN PATENT DOCUMENTS

| 0501322 | 9/1992 | European Pat. Off. |
| WO91/16045 | 10/1991 | WIPO |
| WO93/02677 | 2/1993 | WIPO |
| WO93/03725 | 3/1993 | WIPO |

(List continued on next page.)

OTHER PUBLICATIONS

Drug Actions: Basic Principles and Therapeutic Aspects, Mutschler, E. et al., CRC Press, 1995, pp. 105, 309–12, 173, 325–7, 331, 414, 163, 499, 151 and 142.

Cecil Textbook of Medicine, 19th ed., edited by Wyngaarden, J.B. et al, 1992, pp. 1093–4, 1106–7, 1655–61, 1872–8, 1972–5, 2191–5, 1027–032, 2213–21, 2260 and 127.

Beilstein online data for RN 64057-972.

Clarke et al., Trends in Pharmacological Sciences, 10(10), pp. 385–386 (1989).

(List continued on next page.)

Primary Examiner—C. Warren Ivy
Assistant Examiner—Garth M. Dahlen
Attorney, Agent, or Firm—Charles M. Kinzig; Edward T. Lentz

[57] ABSTRACT

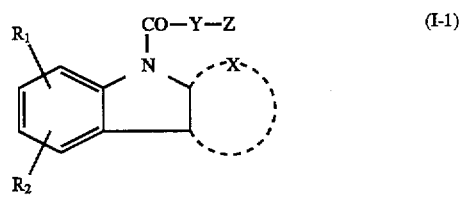

(I-1)

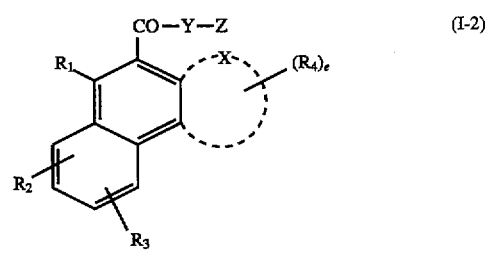

(I-2)

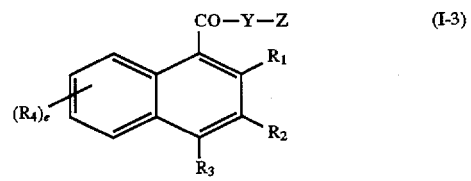

(I-3)

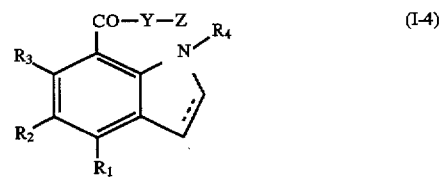

(I-4)

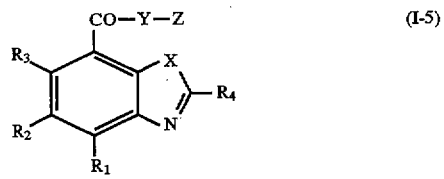

(I-5)

Fused-ring system N-alkylpiperidinyl-4-methyl carboxylic acid ester or amide derivs. and analogues (I), having formula (I-1)-(I-5), and their salts. The variables are defined herein. The compounds (I) are 5-HT4 receptor antagonists, and are useful for treatment or prophylaxis of gastrointestinal, cardiovascular or CNS disorders. Typically (I) are used for treatment of irritable bowel syndrome (including associated diarrhea and urinary incontinence); for treatment of the nausea and gastric symptoms of gastro-oesophageal reflux disease and dyspepsia; as antiemetics (e.g. against cytotoxin agent or radiation-induced emesis); for preventing atrial fibrillation and other atrial arrhythmias and reducing occurrence of stroke; as anxiolytics; and for treatment of migraine, schizophrenia, Parkinson's disease and Huntington's chorea.

10 Claims, No Drawings

FOREIGN PATENT DOCUMENTS

| | | |
|---|---|---|
| WO93/05038 | 3/1993 | WIPO . |
| WO93/05040 | 3/1993 | WIPO . |
| WO93/08187 | 4/1993 | WIPO . |
| WO93/12785 | 7/1993 | WIPO . |
| WO93/14745 | 8/1993 | WIPO . |
| WO93/16072 | 8/1993 | WIPO . |
| WO93/18027 | 9/1993 | WIPO . |
| WO93/18036 | 9/1993 | WIPO . |
| WO93/24117 | 12/1993 | WIPO . |
| WO94/00113 | 1/1994 | WIPO . |
| WO94/05654 | 3/1994 | WIPO . |
| WO94/07859 | 4/1994 | WIPO . |
| WO94/08965 | 4/1994 | WIPO . |
| WO94/08994 | 4/1994 | WIPO . |
| WO94/08995 | 4/1994 | WIPO . |
| WO94/08998 | 4/1994 | WIPO . |
| WO94/10174 | 5/1994 | WIPO . |
| WO94/01095 | 7/1994 | WIPO . |
| WO94/17071 | 8/1994 | WIPO . |
| WO94/19344 | 9/1994 | WIPO . |
| WO94/27987 | 12/1994 | WIPO . |
| WO94/29298 | 12/1994 | WIPO . |
| WO95/04737 | 2/1995 | WIPO . |

OTHER PUBLICATIONS

Clarke et al., Trends in Pharmacological Sciences, 13(4), pp. 141–145 (1992).

Dumuis et al., European J. Pharmacology, vol. 146, pp. 187–188 (1988).

Dumuis et al., Naunyn–Schmiedeberg's Archives of Pharmacology, vol. 340, pp. 403–410 (1989).

N-ALKYLPIPERIDINYL-4-METHYL CARBOXYLIC ESTERS/AMIDES OF CONDENSED RING SYSTEMS AS 5-HT4 RECEPTOR ANTAGONISTS

This application is a 371 of PCT/GB93/02130, Oct. 14, 1993.

This invention relates to novel compounds having pharmacological activity, to a process for their preparation and to their use as pharmaceuticals.

European Journal of Pharmacology 146 (1988), 187–188, and Naunyn-Schmiedeberg's Arch. Pharmacol. (1989) 340:403–410, describe a non classical 5-hydroxytryptamine receptor, now designated the 5-HT$_4$ receptor, and that ICS 205-930, which is also a 5-HT$_3$ receptor antagonist, acts as an antagonist at this receptor. WO 91/16045 (SmithKline and French Laboratories Limited) describes the use of cardiac 5-HT$_4$ receptor antagonists in the treatment of atrial arrhythmias and stroke.

EP-A-501322 (Glaxo Group Limited) describes indole derivatives having 5-HT$_4$ antagonist activity.

WO 93/02677, WO 93/03725, WO 93/05038, WO 93/05040 and WO 93/18036 (SmithKline Beecham plc) describe compounds having 5-HT$_4$ receptor antagonist activity.

It has now been discovered that certain novel compounds also have 5-HT$_4$ receptor antagonist properties.

When used herein, 'treatment' includes prophylaxis as appropriate.

Accordingly, the present invention provides compounds of formula (I), wherein formula (I) consists of formulae (I-1) to (I-5), and pharmaceutically acceptable salts thereof, and the use of a compound of formula (I) or a pharmaceutically acceptable salt thereof:

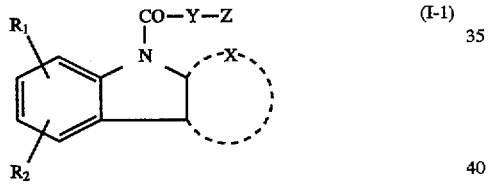
(I-1)

wherein

X and the carbon atoms to which it is attached represents phenyl, cyclohexyl or cyclohexenyl wherein X is —(CH$_2$)$_4$—, and wherein X is optionally substituted by R$_3$ and R$_4$;

R$_1$, R$_2$, R$_3$ and R$_4$ are independently hydrogen, halo, C$_{1-6}$ alkyl, or C$_{1-6}$ alkoxy;

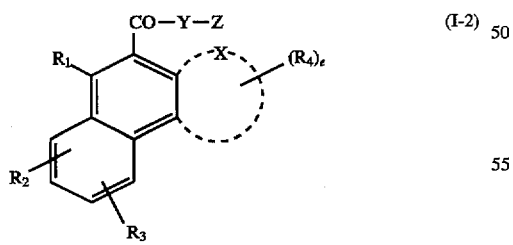
(I-2)

wherein

X is either —X$_1$—(CH$_2$)$_x$—X$_2$— in which X$_1$—(CH$_2$)$_x$—X$_2$ and the aromatic carbon atoms to which they are attached form a 5–7 membered ring wherein one of X$_1$ and X$_2$ is O, S or CH$_2$ and the other is CH$_2$ and x is 1, 2 or 3;

or X is —X$_3$—CH$_2$—CH=CH—, —X$_3$—(CH$_2$)$_2$—CO or —X$_3$—(CH$_2$)$_2$—CH(OR$_x$)— wherein X$_3$ is O or S and R$_x$ is hydrogen or C$_{1-6}$ alkyl;

R$_1$ is hydrogen, halo, C$_{1-6}$ alkyl, C$_{1-6}$ alkoxy or amino;

R$_2$ and R$_3$ are hydrogen, halo, C$_{1-6}$ alkyl or C$_{1-6}$ alkoxy;

R$_4$ is hydrogen or C$_{1-6}$ alkyl and e is 1 or 2;

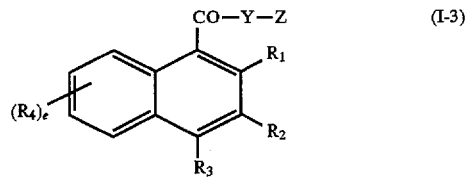
(I-3)

wherein

R$_1$ and R$_2$ are hydrogen, halo, C$_{1-6}$ alkyl or C$_{1-6}$ alkoxy; or

R$_1$ and R$_2$ are together either X$_1$—(CH$_2$)$_x$—X$_2$ in which X$_1$—(CH$_2$)$_x$—X$_2$ and the aromatic carbon atoms to which they are attached form a 5–7 membered ring wherein one of X$_1$ and X$_2$ is O, S or CH$_2$ and the other is CH$_2$ and x is 1, 2 or 3;

or R$_1$ and R$_2$ are together X$_3$—CH$_2$—CH=CH—, X$_3$—(CH$_2$)$_2$—CO or X$_3$—(CH$_2$)$_2$—CH(OR$_x$) wherein X$_2$ is O or S and R$_x$ is hydrogen or C$_{1-6}$ alkyl;

and in which an R$_1$/R$_2$ ring may be optionally substituted by one or two C$_{1-6}$ alkyl groups;

R$_3$ is hydrogen, halo, C$_{1-6}$ alkyl, C$_{1-6}$ alkoxy or amino;

R$_4$ is hydrogen, halo, C$_{1-6}$ alkyl or C$_{1-6}$ alkoxy and e is 1 or 2;

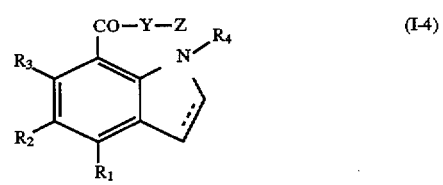
(I-4)

wherein

--- represents a single or double bond;

R$_1$ is hydrogen, amino, halo, C$_{1-6}$ alkyl, hydroxy or C$_{1-6}$ alkoxy;

R$_2$ is hydrogen, halo, C$_{1-6}$ alkyl, C$_{1-6}$ alkoxy, nitro, amino or C$_{1-6}$ alkylthio;

R$_3$ is hydrogen, halo, C$_{1-6}$ alkyl, C$_{1-6}$ alkoxy or amino;

R$_4$ is hydrogen or C$_{1-6}$ alkyl;

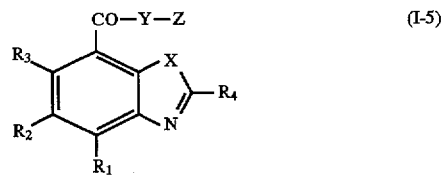
(I-5)

wherein

X is O or S;

R$_1$ is hydrogen, amino, halo, C$_{1-6}$ alkyl, hydroxy or C$_{1-6}$ alkoxy;

R$_2$ is hydrogen, halo, C$_{1-6}$ alkyl, C$_{1-6}$ alkoxy, nitro, amino or C$_{1-6}$ alkylthio;

R$_3$ is hydrogen, halo, C$_{1-6}$ alkyl, C$_{1-6}$ alkoxy or amino;

R$_4$ is hydrogen or C$_{1-6}$ alkyl;

In formulae (I-1) to (I-5) inclusive:

Y is O or NH;

Z is of sub-formula (a), (b) or (c):

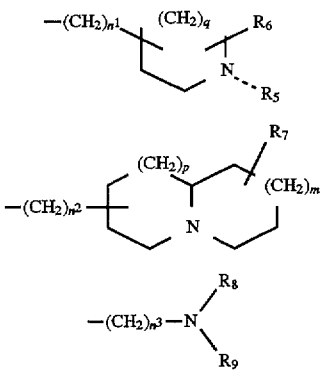

wherein $n^1$ is 0, 1, 2, 3 or 4; $n^2$ is 0, 1, 2, 3 or 4; $n^3$ is 2, 3, 4 or 5;

q is 0, 1, 2 or 3; p is 0, 1 or 2; m is 0, 1 or 2;

$R_5$ is hydrogen, $C_{1-12}$ alkyl, aralkyl or $R_5$ is $(CH_2)_z$—$R_{10}$ wherein z is 2 or 3 and $R_{10}$ is selected from cyano, hydroxyl, $C_{1-6}$ alkoxy, phenoxy, $C(O)C_{1-6}$ alkyl, $COC_6H_5$, —$CONR_{11}R_{12}$, $NR_{11}COR_{12}$, $SO_2NR_{11}R_{12}$ or $NR_{11}SO_2R_{12}$ wherein $R_{11}$ and $R_{12}$ are hydrogen or $C_{1-6}$ alkyl; and $R_6$, $R_7$ and $R_8$ are independently hydrogen or $C_{1-6}$ alkyl; and $R_9$ is hydrogen or $C_{1-10}$ alkyl;

or a compound of formula (I) wherein the CO—Y linkage is replaced by a heterocyclic bioisostere;

in the manufacture of a medicament having 5-HT$_4$ receptor antagonist activity.

Examples of alkyl or alkyl containing groups include $C_1$, $C_2$, $C_3$, $C_4$, $C_5$, $C_6$, $C_7$, $C_8$, $C_9$, $C_{10}$, $C_{11}$ or $C_{12}$ branched, straight chained or cyclic alkyl, as appropriate. $C_{1-4}$ alkyl groups include methyl, ethyl, n- and iso-propyl, n-, iso-, sec- and tert-butyl. Cyclic alkyl includes cyclopropyl, cyclobutyl, cyclopentyl, cyclohexyl, cycloheptyl and cyclooctyl.

Aryl includes phenyl and naphthyl optionally substituted by one or more substituents selected from halo, $C_{1-6}$ alkyl and $C_{1-6}$ alkoxy.

Halo includes fluoro, chloro, bromo and iodo.

In formula (I-2):

X is often O and A represents a single bond.

$R_1$ is preferably methoxy.

$R_2$ is preferably hydrogen or halo.

$R_3$ is preferably hydrogen or halo.

$R_4$ is often hydrogen.

In formula (I-4):

$R_1$ is preferably hydrogen or amino.

$R_2$ is preferably hydrogen or halo.

$R_3$ is preferably hydrogen or halo.

$R_4$ is often hydrogen.

In formula (I-5):

$R_1$ is preferably hydrogen or amino.

$R_2$ is preferably hydrogen or halo.

$R_3$ is preferably hydrogen or halo.

$R_4$ is often hydrogen.

A suitable bioisostere for the amide or ester linkage containing Y in formula (I), is of formula (d):

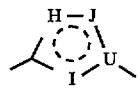

wherein the dotted circle represents one or two double bonds in any position in the 5-membered ring; H, J and I independently represent oxygen, sulphur, nitrogen or carbon, provided that at least one of H, J and I is other than carbon; U represents nitrogen or carbon.

Suitable examples of (d) are as described for X, Y and Z in EP-A-328200 (Merck Sharp & Dohme Ltd.), such as an oxadiazole moiety.

Y is preferably O or NH.

When Z is of sub-formula (a), $n^1$ is preferably 2, 3 or 4 when the azacycle is attached at the nitrogen atom and $n^1$ is preferably 1 when the azacycle is attached at a carbon atom, such as the 4-position when q is 2.

When Z is of sub-formula (b), $n^2$ is preferably such that the number of carbon atoms between the ester or amide linkage is from 2 to 4 carbon atoms.

Suitable values for p and m include p=m=1; p=0, m=1, p=1, m=2, p=2, m=1.

When Z is of sub-formula (c), $n^3$ is preferably 2, 3 or 4.

$R_8$ and $R_9$ are preferably both alkyl, especially one of $R_8$ and $R_9$ is $C_4$ or larger alkyl.

Specific values of Z of particular interest are as follows:

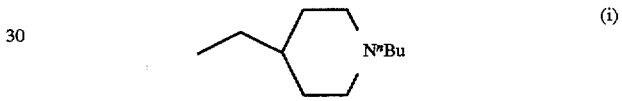

(i)

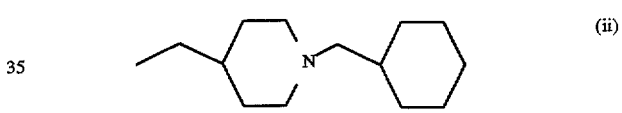

(ii)

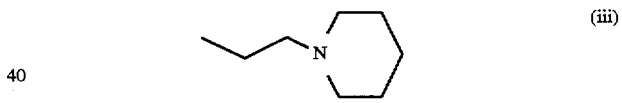

(iii)

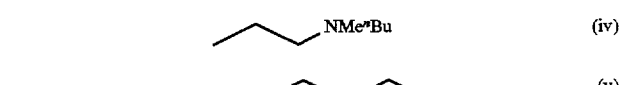

(iv)

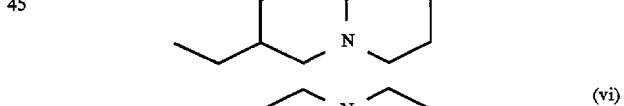

(v)

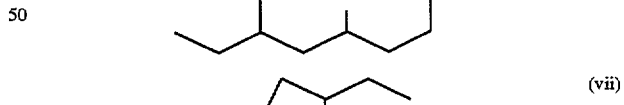

(vi)

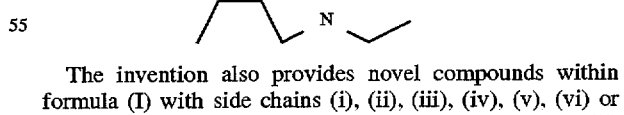

(vii)

The invention also provides novel compounds within formula (I) with side chains (i), (ii), (iii), (iv), (v), (vi) or (vii). In a further aspect, the piperidine ring in (i), (ii) or (iii) may be replaced by pyrrolidinyl or azetidinyl, and/or the N-substituent in (i) or (ii) may be replaced by $C_3$ or larger alkyl or optionally substituted benzyl.

In an alternative aspect, the N-substituent in formula (i) or (ii) may be replaced by $(CH_2)_nR^4$ as defined in formula (I) and in relation to the specific examples of EP-A-501322.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

Examples of pharmaceutically acceptable salts include quaternary derivatives of the compounds of formula (I) such as the compounds quaternised by compounds $R_x$-T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

The compounds of formula (I) wherein CO—Y is an ester or amide linkage are prepared by conventional coupling of the Z moiety with the appropriate acid. Suitable methods are as described in GB 2125398A (Sandoz Limited), GB 1593146A, EP-A-36269, EP-A-289170 and WO 92/05174 (Beecham Group p.l.c.). When CO—Y is replaced by a heterocyclic bioisostere, suitable methods are described in EP-A-328200 (Merck Sharp & Dohme Limited). Reference is also made to EP-A-501322 (Glaxo Group Limited).

The invention also comprises a process for preparing the novel compounds of formula (I) which comprises reacting an appropriate acid derivative with an appropriate alcohol or amine. A process comprises reacting an acid derivative wherein the aromatic substituents are as required in the end compound of formula (I), or substituents convertible thereto, with an alcohol or amine containing Z or a group convertible thereto, and thereafter if necessary, converting the benzoic acid substituents and/or Z, and optionally forming a pharmaceutically acceptable salt.

Suitable examples of conversions in the aromatic substituents include chlorination of hydrogen to chloro, reduction of nitro to amino, dehydrohalogenation such as debromination. Any elaboration is, however, usually carried out prior to ester or amide coupling.

Suitable examples of conversions in the Z containing moiety include conventional modifications of the N-substituent by substitution and/or deprotection or, in the case of a 2-, 3- or 4- substituted piperidinyl desired end compound, reduction of an appropriate pyridyl derivative.

The compounds of the present invention are 5-HT$_4$ receptor antagonists and it is thus believed may generally be used in the treatment or prophylaxis of gastrointestinal disorders, cardiovascular disorders and CNS disorders.

They are of potential interest in the treatment of irritable bowel syndrome (IBS), in particular the diarrhoea aspects of IBS, i.e., these compounds block the ability of 5-HT to stimulate gut motility via activation of enteric neurones. In animal models of IBS, this can be conveniently measured as a reduction of the rate of defaecation. They are also of potential use in the treatment of urinary incontinence which is often associated with IBS.

They may also be of potential use in other gastrointestinal disorders, such as those associated with upper gut motility, and as antiemetics. In particular, they are of potential use in the treatment of the nausea and gastric symptoms of gastro-oesophageal reflux disease and dyspepsia. Antiemetic activity is determined in known animal models of cytotoxic-agent/radiation induced emesis.

Specific cardiac 5-HT$_4$ receptor antagonists which prevent atrial fibrillation and other atrial arrhythmias associated with 5-HT, would also be expected to reduce occurrence of stroke (see A. J. Kaumann 1990, Naumyn-Schmiedeberg's Arch. Pharmacol. 342, 619–622, for appropriate animal test method).

Anxiolytic activity is likely to be effected via the hippocampus (Dumuis et al 1988, Mol Pharmacol., 34, 880–887). Activity can be demonstrated in standard animal models, the social interaction test and the X-maze test.

Migraine sufferers often undergo situations of anxiety and emotional stress that precede the appearance of headache (Sachs, 1985, Migraine, Pan Books, London). It has also been observed that during and within 48 hours of a migraine attack, cyclic AMP levels are considerably increased in the cerebrospinal fluid (Welch et al., 1976, Headache 16, 160–167). It is believed that a migraine, including the prodomal phase and the associated increased levels of cyclic AMP are related to stimulation of 5-HT$_4$ receptors, and hence that administration of a 5-HT$_4$ antagonist is of potential benefit in relieving a migraine attack.

Other CNS disorders of interest include schizophrenia, Parkinson's disease and Huntingdon's chorea.

The invention also provides a pharmaceutical composition comprising a compound of formula (I), or a pharmaceutically acceptable salt thereof, and a pharmaceutically acceptable carrier.

Such compositions are prepared by admixture and are usually adapted for enteral such as oral, nasal or rectal, or parenteral administration, and as such may be in the form of tablets, capsules, oral liquid preparations, powders, granules, lozenges, reconstitutable powders, nasal sprays, suppositories, injectable and infusable solutions or suspensions. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of irritable bowel syndrome, dyspepsia, atrial arrhythmias and stroke, anxiety and/or migraine in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.5 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated within the aforementioned dosage ranges.

The invention also provides a compound of formula (I) or a pharmaceutically acceptable salt thereof for use as an active therapeutic substance, in particular for use in the treatment of irritable bowel syndrome, gastro-oesophageal reflux disease, dyspepsia, atrial arrhythmias and stroke, anxiety and/or migraine.

The following Examples illustrates the preparation of compounds of formula (I), and the following Descriptions relate to the preparation of intermediates. The compounds of formula (I-1) and intermediates are prepared in Examples and Descriptions 1-1, 2-1 etc, the compounds of formula (I-2) are prepared in Examples and Descriptions 1-2, 2-2 etc and similarly for the compounds of formulae (I-3) to (I-5).

It will be appreciated that any compound prepared wherein Y is O may be provided as the corresponding compound wherein Y is NH.

EXAMPLE (1-1)

[$R_1$, $R_2$, $R_3$, $R_4$, H, X is cyclohexyl, Y=O, Z=(i)]

N-Carboxy-[1-butyl-4-piperidinylmethyl]-1,2,3,4,4a,9a-hexahydrocarbazole

1-Butyl-4-piperidinylmethanol (0.500 g 2.12 mmol) was dissolved in dry THF (3 ml) and treated with methyllithium (1.5M solution in diethyl ether) 2.16 ml, 2.33 mmol) with stirring under nitrogen. After 10 minutes, N-chlorocarbonyl-1,2,3,4,4a,9a-hexahydrocarbazole (0.630 g, 2.68 mmol) (Ref: WO 89/09217) in dry THF (5 ml) was added dropwise with stirring. After 48 hours, the reaction mixture was filtered and the filtrate evaporated under reduced pressure. The residue was purified by silica-gel chromatography, eluting with 2% MeOH/CHCl$_3$-3%MeOH/CHCl$_3$ to give the title compound as a clear, colourless oil, which was converted to the oxalate salt, nap 187°–189° C.

$^1$H NMR (250 MHz, CDCl$_3$) (free base)

δ:7.90-7.60 (s br, 1H) 7.25-7.10 (m, 2H), 7.00 (t, 1H), 4.45-4.30 (m br, 1H), 4.10 (d, 2H), 3.45 (t, 1H), 3.00 (d, 2H), 2.45-2.20 (m, 3H), 2.10-1.95 (m, 3H),1.85-1.70 (m, 4H), 1.65-1.40 (m, 6H), 1.40-1.10 (m, 6H), 0.90 (t, 3H).

EXAMPLES 2-1 AND 3-1

[$R_1$, $R_2$, $R_3$, $R_4$,=H, X is cyclohexenyl/phenyl, X=O, Z=(i)]

N-Carboxy-[1-butyl-4-piperidinylmethyl]-1,2,3,4-tetrahydrocarbazole

N-Carboxy-[1-butyl-4-piperidinylmethyl]-carbazole

N-Carboxy-[1-butylpiperidin-4-ylmethyl]-1,2,3,4,4a,9a-hexahydrocarbazole (0.530 g, 1.32 mmol) was dissolved in chloroform (25 ml) and treated with 2,3-dichloro-5,6-dicyano-1, 4-benzoquinone (0.329 g, 1.58 mmol) with stirring. The mixture was heated to reflux for 12 hours, cooled, and more 2,3-dichloro-5,6-dicyano-1,4-benzoquinone (0.329 g 1.58 mmol) added with stirring. The mixture was heated to reflux for 12 hours, cooled and evaporated under reduced pressure. The residue was purified by Silica-gel chromatography, eluting with 2%MeOH/CHCl$_3$ to give the title compounds as 3:1 mixture. The mixture was separated by preparative HPLC using a Waters Micro Bondapak C$_{18}$ (300 mm×7.8 mm) column and eluting with 75:25 MeCN: 0.1M Ammonium Acetate (pH 5.0).

(2-1) 1H NMR (400 MHz, CDCl$_3$)

δ:8.10 (d, 1H), 7.40 (d, 1H), 7.28-7.18 (m, 2H), 4.28 (d, 2H), 3.03-2.95 (m.4H),2.68-2.62 (m, 2H), 2.35 (t, 2H), 2.00-1.80 (m, 5H), 1.53-1.38 (m, 4H), 1.35-1.25 (m, 3H), 0.92 (t, 3H).

(3-1) 1H NMR (400 MHz, CDCl$_3$)

δ: 8.28 (d, 2H), 8.00 (d, 2H), 7.50 (t, 2H), 7.38 (t, 2H), 4.48 (d, 2H), 3.05-2.95 (m, 4H), 2.65-2.60 (m, 2H), 2.35 (t, 2H), 2.00-1.75 (m,5H), 1.40-1.30 (m, 3H), 0.95 (t, 3H).

EXAMPLE 1-2

[$R_1$, $R_2$, $R_3$, $R_4$,=H, X=O—(CH$_2$)$_3$—, Y=O, Z=(i)]

1-Butylpiperidin-4-ylmethyl-3,4-dihydro-2H-naphtho[2,1-b]pyran-10-carboxylate 3,4-Dihydro-2H-naphtho[2,1-b]pyran-10-carboxylic acid (0.510 g, 2.24 mmol) was dissolved in CH$_2$Cl$_2$ (20 ml) and treated with oxalyl chloride (0.292 ml, 3.35 mmol), followed by a drop of dry DMF with stirring under $N_2$. After 3 h, the reaction mixture was evaporated under reduced pressure and dried in vacuo to give the crude acid chloride. Meanwhile, a solution of 1-butylpiperidin-4-yl methanol (0.363 g, 2.12 mmol) in dry THF (10 nil) was treated with 1.5M methyl-lithium (1.12 ml, 2.12 mmol). After 0.25 h to this solution was added the crude acid chloride in dry THF (10 ml) with stirring under $N_2$. After 40 h, the reaction mixture was evaporated under reduced pressure and the residue partitioned between EtOAc and water. The aqueous layer was then extracted with EtOAc (1×) and the combined organic layers were dried ($Na_2SO_4$) and evaporated under reduced pressure to give a yellow oil which was purified by silica gel chromatography (EtOAc as eluant) to give the title compound as a pale yellow oil (0.180 g, 21%) which was converted to its hydrochloride salt m.p. (HCl salt) 137°–139° C.

1H NMR ($CDCl_3$) 250 MHz (free base)

δ: 8.14(1H,s), 7.80(2H,m), 7.58(1H, t, J=7 Hz), 7.40(1H, t, J=7 Hz), 4.30(2H, t, J=6 Hz), 4.20(2H, d, J=6 Hz), 3.08(2H, t, J=6 Hz), 2.98(2H, d, J=12 Hz), 2.35(2H, t, J=6 Hz), 2.20(2H,m), 2.00-1.70(6H, m), 1.60-1.25(5H,m), 0.92 (3H, t, J=6 Hz)

EXAMPLE 2-2

[$R_1$, $R_2$, $R_3$, $R_4$,=H, X=O—$CH_2$—CH=CH—, Y=O, Z=(i)],

1-Butylpiperidin-4-ylmethyl-2H-naphtho[2,1-b]pyran-10-carboxylate

This was prepared from 2H-naphtho[2,1-b]pyran-10-carboxylic acid using the method outlined in Example 1.

$^1$H NMR ($CDCl_3$) 200 MHz

δ: 8.20(1H,s), 7.90(1H,d,J=8 Hz), 7.80(1H,d, J=8 Hz), 7.55(1H, t, J=8 Hz), 7.40(1H,t,J=8 Hz), 7.10(1H, d, J=12 Hz), 6.00 (1H, m), 4.92(2H, m), 4.20(2H, d, J=6 Hz), 3.00(2H, d, J=12 Hz), 2.35(2H, t, J=6 Hz), 2.05-1.75(5H,m), 1.60-1.32(6H, m), 0.95(3H, t, J=6 Hz).

DESCRIPTION 1-2

(Intermediate for Example 1-2)

a) Methyl-3-propargyloxy-2-naphthoate

Methyl-3-hydroxy-2-naphthoate (2.63 g, 0.013 mol) was dissolved in dry THF (80 ml) and treated with sodium hydride (80%) ((0.398 g, 0.013 mol), with stirring under $N_2$. After 0.5 h, propargyl bromide (80% in toluene) (2.57 ml 0.017 mol) was added and the mixture heated to reflux. After 20 h, the reaction mixture was allowed to cool and then evaporated under reduced pressure. The residue was then evaporated under reduced pressure. The residue was then partitioned between EtOAc and water. The aqueous layer was then extracted with EtOAc (1×), and the combined organic layers were dried ($Na_2SO_4$) and evaporated to given an orange oil. Crystallisation of the oil from petrol (60/80) diethyl ether provided the title compound as a pale yellow solid (1.0 gg, 35%).

$^1$H NMR ($CDCl_3$) 250 MHz

δ: 8.34(1H, s), 7.80(1H,dd, J=16 and 8 Hz), 7.53(1H, t, J=8 Hz), 7.40(1H, t,J=8 Hz), 4.90(2H, d,J=1 Hz), 3.95(3H, s), 2.57(1H, t, J=1 Hz)

b) Methyl-2H-naphtho[2,1-b]pyran-10-carboxylate

Methyl-3-propargyloxy-2-naphthoate (D1) (1.00 g, 4.17 mmol) was dissolved in 1,2,dichlorobenzene (50 ml) and heated to reflux under $N_2$ with stirring. After 64 h, the reaction mixture was allowed to cool and was then evaporated under reduced pressure. The brown oily residue was then purified by silica-gel chromatography (Pentane: EtOAc 4:1 as eluant) to give the title compound to an orange oil (0.801 g, 80%).

$^1$H NMR ($CDCl_3$) 250 MHz

δ: 8.20(1H,s), 7.92(1H, d, J=8 Hz), 7.80(1H, d, J=8 Hz), 7.54 (1H, t, J=8 Hz), 7.40(1H,t,J=8 Hz), 7.12(1H, d,J=8 Hz), 6.00(1H,m), 4.94(2H,m), 3.94(3H,s)

c) Methyl-3,4-dihydro-2H-naphtho[2, 1-b]pyran-10-carboxylate

Methyl-2H-naphtho[2, 1-b]pyran-10-carboxylate (0.590 g, 2.46 mmol) was dissolved in ethyl acetate (30 ml) and 5% PdC (0.2 g) was added under $N_2$. The mixture was then hydrogenated at atmospheric pressure. When theoretical $H_2$ uptake had been achieved, the reaction mixture was flushed with $N_2$ and then filtered through a pad of celite. The filtrate was then evaporated under reduced pressure and dried in vacuo to give the title compound as a pale yellow oil (0.154 g, 91%).

$^1$H NMR ($CDCl_3$) 200 MHz

δ:8.20 (1H, s), 7.82 (1H, d, J=8 Hz), 7.58(1H, t, J=8 Hz), 7.40(1H, t, J=8 Hz), 4.37(2H, t, J=6 Hz), 3.98(3H, s), 3.12(2H, t, J=6 Hz), 2.25(2H,m).

d) 3,4-Dihydro-2H-naphtho[2.1-b]pyran-10-carboxylic acid

Methyl-2H-3,4,dihydronaphtho[2.1-b]pyran-10-carboxylate (0.530 g, 2.19 mmol) was dissolved in ethanol (15 ml) and 10% NaOH (15 ml) was added. The mixture was then heated to reflux with stirring. After 6 h, the reaction mixture was allowed to cool and the ethanol present was removed by evaporation under reduced pressure. The aqueous residue was then acidified to pH 1 using conc. hydrochloric acid and the resultant oily suspension was extracted with $CHCl_3$ (3×). The combined organic layers were then dried ($Na_2SO_4$) and evaporated under reduced pressure to give a pale yellow oil that crystallised on standing (0.499 g, 100%).

$^1$H NMR ($CDCl_3$) 200 MHz

δ:12.0-10.5 br(1H,s), 8.60(1H,s), 7.87(1H, d, J=8 Hz), 7.78(1H, d, J=8 Hz), 7.58(1H, t, J=8 Hz), 7.38(1H, t, J=8 Hz) 4.44(2H, t, J=6 Hz), 3.12(2H, t, J=6 Hz), 2.25(2H,m).

DESCRIPTION 2-2

(Intermediate for Example 2-2)

2H-Naphtho[2,1-b]pyran-10-carboxylic acid

This was prepared from methyl-2H-naphtho[2, 1-b]pyran-10-carboxylate using the method outlined in Description 1-2d).

$^1$H NMR ($CDCl_3$) 200 MHz

δ: 8.60(1H,s), 7.90(2H,m), 7.60(1H,t,J=8Hz), 7.40(1H, t, J=8 Hz), 7.15 (1H, d, J=12 Hz), 6.08 (1H, m), 5.05(2H,m)

EXAMPLE 1-3

[$R_1$, $R_2$, $R_3$, $R_4$,=H, Y=O, Z=(i)]

[1-Butylpiperidin-4-ylmethylnaphthalene-1-carboxylate

To a slurry of 1-naphthoic acid (500 mg) in dichloromethane (30 ml) was added oxalyl chloride (510 ml) and N,N' dimethylformamide (2 drops). The resulting mixture was stirred at room temperature for 1 hour. The solvent was concentrated in vacuo to afford crude acid chloride. Methyllithium (2.14 ml of 1.5M soln. in diethyl ether) was added dropwise to a solution of 1-butyl-4-hydroxymethylpiperidine (500 mg) in dry THF (10 ml) at 0° C. Stirring was continued at 0° C. for 10 minutes. A solution of crude acid chloride in THF (10 ml) was added to the reaction mixture and stirring continued at room temperature overnight. Water (2 ml) was added and the solvent concentrated under reduced pressure. The residue was partitioned between chloroform and water. The organic phase was dried ($Na_2SO_4$), filtered and concentrated in vacuo. The residue was chromatographed on silica using chloroform and ethanol as eluant to afford pure ester (502 mg). Treatment with ethereal HCl gave the title compound as a solid.

$^1$H NMR$_{250}$ MHz (CDCl$_3$) Free base

δ: 8.92(d, 1H), 8.19(d,1H), 8.03(d,1H), 7.89(d,1H), 7.44–7.65(m,3H), 4.28(d,2H), 2.99(d,2H), 2.32(t,2H), 1.71–2.02(m,5H), 1.43–1.58(m,4H), 1.23–1.41(m,2H), 0.9 (t,3H).

EXAMPLE 1-4

[- - - is single bond, $R_1$, $R_2$, $R_3$, $R_4$=H, Y=O, Z=(i)]

7-(1-Butyl-4-piperidinylmethyl)-1H-2,3-dihydroindolecarboxylate

Indoline-7-carboxylic acid (Ger. Offen. 2,117,116) is coupled with lithium-(1-butyl-4-piperidinyl)methoxide via the imidazolide The following compounds are prepared similarly, using the appropriate acid:

EXAMPLE 2-4

[- - - is single bond, $R_1$=H, $R_2$=Cl, $R_3$, $R_4$=H, Y=O, Z=(i)]

[7-(1-Butyl-4-piperidinylmethyl)-5-chloro-1H-2,3-dihydroindolecarboxylate

EXAMPLE 2-4

[- - - is double bond, $R_1$, $R_2$, $R_3$, $R_4$=H, Y=O, Z=(i)]

7-(1-Butyl-4-piperidinylmethyl)-1H-indolecarboxylate

EXAMPLE 4-4

[- - - is double bond, $R_1$=H, $R_2$=Cl, $R_3$, $R_4$=H, Y=O, Z=(i)]

7-(1-Butyl-4-piperidinylmethyl)-5-chloro-1 H-indolecarboxylate

DESCRIPTION 1-5

N-(1-Butyl-4-piperidinyl)methylamine

A stirred solution of isonipecotamide (70 g, 0.55 mole) and 1-bromobutane (58.8 ml, 0.55 mole) in ethanol (700 ml) was treated with anhydrous potassium carbonate (152 g, 1.10 mole) and heated under reflux for 3 h. The mixture was allowed to cool, then filtered and the filtrate concentrated under vacuum. The residual oil was dissolved in chloroform (400 ml) and washed with water (1×300 ml), then dried ($Na_2SO_4$) and concentrated under vacuum to leave a yellow oil (77.5 g). This oil was mixed thoroughly with phosphorus pentoxide (75 g) and the mixture heated at 160°–180° C. under nitrogen for 2.5 h with gentle stirring. The reaction mixture was allowed to cool, then treated with water (500 ml). When the solid mass had dissolved, the solution was basified by addition of solid $K_2CO_3$ and extracted with ethyl acetate (2×400 ml). The combined extracts were dried ($Na_2SO_4$) and concentrated in vacuo to leave a brown oil (78 g). This was dissolved in dry ether (400 ml) and added dropwise over 30 minutes to a stirred suspension of lithium aluminium hydride (25 g, 0.66 mole) in ether (200 ml) at 0° C under nitrogen. When addition was complete, the mixture was allowed to warm up to room temperature and stir for 18 h. It was re-cooled to 0° C and treated cautiously with water (25 ml), 10% NaOH solution (25 ml) and water again (75 ml). The mixture was filtered through kieselguhr and the filtrate concentrated in vacuo to leave a brown oil, which was distilled under vacuum to afford the title compound as a colourless oil (66 g, 71%) bp 96°–99° C. at 3 mm Hg.

$^1$H NMR (CDCl$_3$)

δ: 2.90–3.02(m,2H), 2.58(d,2H), 2.25–2.38(m,2H), 1.65–2.00(m,4H), 1.08–1.58(m,9H), 0.92(t,3H).

EXAMPLE 1-5

[$R_1$=H, $R_2$=Cl, $R_3$, $R_4$,=H, Y=O, Z=(i)]

N-[(1-Butyl-4-piperidinyl)methyl]5-chloro-2-methylbenzoxazole-7-carboxamide

5-Chloro-2-methylbenzoxazole-7-carboxylic acid (Ger. Offen. 2,225,544) is converted to its acid chloride by treatment with oxalyl chloride. The acid chloride is treated with N-(1-butyl-4-piperidinyl)methylamine in the presence of triethylamine to afford the title compound.

5-HT$_4$ RECEPTOR ANTAGONIST ACTIVITY

1) Guinea pig colon

Male guinea-pigs, weighing 250–400 g are used. Longitudinal muscle-myenteric plexus preparations, approximately 3 cm long, are obtained from the distal colon region. These are suspended under a 0.5 g load in isolated tissue baths containing Krebs solution bubbled with 5% $CO_2$ in $O_2$ and maintained at 37° C. In all experiments, the Krebs solution also contains methiothepin $10^{-7}$M and granisetron $10^{-6}$M to block effects at 5-HT$_1$, 5-HT$_2$ and 5-HT$_3$ receptors.

After construction of a simple concentration-response curve with 5-HT, using 30s contact times and a 15 min dosing cycle, a concentration of 5-HT is selected so as to obtain a contraction of the muscle approximately 40–70% maximum($10^{-9}$M approx). The tissue is then alternately dosed every 15 min with this concentration of 5-HT and then with an approximately equi-effective concentration of the nicotine receptor stimulant, dimethylphenylpiperazinium (DMPP). After obtaining consistent responses to both 5-HT and DMPP, increasing concentrations of a putative 5-HT$_4$ receptor antagonist are then added to the bathing solution. The effects of this compound are then determined as a percentage reduction of the contractions evoked by 5-HT or by DMPP. From this data, pIC$_{50}$ values are determined, being defined as the -log concentration of antagonist which reduces the contraction by 50%. A compound which reduces the response to 5-HT but not to DMPP is believed to act as a 5-HT$_4$ receptor antagonist.

The compounds generally had a pIC$_{50}$ of at least 7.

We claim:

1. Compounds of formula (I-1) or a pharmaceutically acceptable salt thereof:

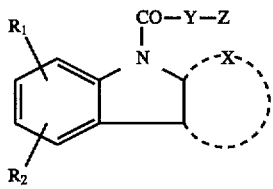

wherein

X and the carbon atoms to which it is attached represents phenyl, cyclohexyl or cyclohexenyl optionally substituted by $R_3$ and $R_4$;

$R_1$, $R_2$, $R_3$ and $R_4$ are independently hydrogen, halo, $C_{1-6}$ alkyl, or $C_{1-6}$ alkoxy;

wherein

Y is O or NH;

Z is of sub-formula (a)

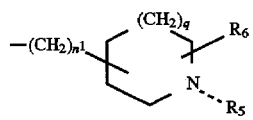

wherein $n^1$ is 1 and the azacycle is attached at the 4-position;

q is 1;

$R_5$ is hydrogen, $C_{1-12}$ alkyl, aralkyl or $R_5$ is $(CH_2)_z$—$R_{10}$ wherein z is 2 or 3 and $R_{10}$ is selected from cyano, hydroxyl, $C_{1-6}$ alkoxy, phenoxy, $C(O)C_{1-6}$ alkyl, $COC_6H_5$, —$CONR_{11}R_{12}$, $NR_{11}COR_{12}$, $SO_2NR_{11}R_{12}$ or $NR_{11}SO_2R_{12}$ wherein $R_{11}$ and $R_{12}$ are hydrogen or $C_{1-6}$ alkyl; and $R_6$ is hydrogen or $C_{1-6}$ alkyl;

or a compound of formula (I-1) wherein the CO—Y linkage is replaced by a heterocyclic bioisostere.

2. A compound according to claim 1 wherein Z is N-substituted 4-piperidylmethyl.

3. A compound according to claim 2 wherein the N-substituent is $C_2$ or greater alkyl, or optionally substituted benzyl.

4. N-Carboxy-[1-butyl-4-piperidinylmethyl]-1,2,3,4,4a,9a-hexahydrocarbazole, a compound which is N-carboxy-[1-butyl-4-piperidinylmethyl]-1,2,3,4-tetrahydrocarbazole, or N-carboxy-[1-butyl-4-piperidinylmethyl]-carbazole.

5. A compound according to claim 1 but wherein Y is NH.

6. A pharmaceutical composition comprising a compound according to claim 1, and a pharmaceutically acceptable carrier.

7. A method for treating irritable bowel syndrome (IBS) which comprises administering a compound according to claim 1.

8. A method for treating urinary incontinence which comprises administering a compound according to claim 1.

9. A method for treating atrial arrhythmia or stroke which comprises administering a compound according to claim 1.

10. A method of treating anxiety, migraine, schizophrenia, Parkinson's disease and Huntingdon's chorea, which comprises administering a compound according to claim 1.

* * * * *